United States Patent
Gorman et al.

(10) Patent No.: US 6,525,180 B1
(45) Date of Patent: Feb. 25, 2003

(54) ANTIBODIES TO MAMMALIAN T CELL SURFACE ANTIGEN

(75) Inventors: Daniel M. Gorman, Newark, CA (US); Jeanine D. Mattson, San Francisco, CA (US)

(73) Assignee: Schering Corporation, Kenilworth, NJ (US)

(*) Notice: Subject to any disclaimer, the term of this patent is extended or adjusted under 35 U.S.C. 154(b) by 0 days.

(21) Appl. No.: 09/671,658

(22) Filed: Sep. 27, 2000

Related U.S. Application Data

(63) Continuation of application No. 08/989,362, filed on Dec. 12, 1997, now Pat. No. 6,242,586.
(60) Provisional application No. 60/032,846, filed on Dec. 13, 1996.

(51) Int. Cl.$^7$ .......................... C07K 16/18; C07K 16/28
(52) U.S. Cl. .............................. 530/388.75; 530/387.1; 530/387.9; 530/388.1; 530/388.2; 530/388.22; 530/388.7; 530/388.73; 530/389.1; 530/389.6; 530/391.1; 530/391.3; 530/391.7
(58) Field of Search ........................... 530/387.9, 388.1, 530/389.1, 387.1, 388.2, 388.22, 388.7, 388.73, 388.75, 389.6, 391.1, 391.3, 391.7

(56) References Cited

U.S. PATENT DOCUMENTS

| 5,759,804 A | 6/1998 | Godiska et al. |
| 5,843,678 A | 12/1998 | Boyle et al. |
| 6,015,938 A | 1/2000 | Boyle et al. |

FOREIGN PATENT DOCUMENTS

| EP | 0 911 342 A1 | 4/1999 |
| WO | WO 98/28426 | 7/1998 |
| WO | WO 96/31625 | 10/1998 |
| WO | WO 98/46751 | 10/1998 |

OTHER PUBLICATIONS

Ngo et al.; in The Protein Folding Problem and Tertiary Structure Prediction, 1994, Merz et al., (ed.), Birkhauser, Boston, MA, pp. 433 and 492–495.*
Coleman et al. (Research in Immunology, 1994; 145(1): 33–36).*
Abaza et al. (Journal of Protein Chemistry, vol. 11, No. 5, 1992, pp. 433–444).*
Lederman et al. (Molecular Immunology 28: 1171–1181, 1991).*
Li et al. (PNAS 77: 3211–3214, 1980).*
Dirk M. Anderson, et al., *Nature*, 390:175–179, Nov. 13, 1998. "A homologue of the TNF receptor and its ligand enhance t–cell growth and dendritic–cell function".
Richard J. Armitage, *Current Opinion in Biology*, 6:407–413, 1994. "Tumor necrosis factor receptor superfamily members and their ligands".
Stacey J. Baker and E. Premkumar Reddy, *Oncogene*, 12:1–9, 1996. "Transducers of life and death: TNF receptor superfamily and associated proteins".
J.W. Ellison, et al., *Mammalian Genome*, 7:25–30, 1996. "Rapid evolution of human pseudoautosomal genes and their mouse homologs".
Hans–Jürgen Gruss and Steven K. Dower, *Blood*, 85(12):3378–3404, Jun. 15, 1995. "Tumor Necrosis Factor Ligand Superfamily: Involvment in the Pathology of Malignant Lymphomas".
D.L. Lacey, et al., *Cell*, 93:165–176, Apr. 17, 1998. "Osteoprotegerin Ligand Is a Cytokine that Regulates Osteoclast Differentiation".
K. Matsubara and K. Okubo, *GCG Geneseq Database Entry*, Accession No. T26135, Oct. 18, 1996. "Human gene signature HUMGS08372".
Erin Murphy, et al., *J. Exp. Med.* 183: 901–913, Mar. 1996. "Reversibility of T Helper 1 and 2 Populations Is Lost After Long–term Stimulation".
Craig A. Smith, et al., *Cell*, 76:959–962, Mar. 26, 1994. "The TNF Receptor Superfamily of Cellular and Viral Proteins: Activation, Costimulation, and Death".
Peter Openshaw, et al., *J. Exp. Med.* 182:1357–1367, Nov. 1995. "Heterogeneity of Intracellular Cytokine Synthesis at the Single–Cell Level in Polarized T Helper 1 and T Helper 2 Populations".
Stephen R. Wiley, et al., *Immunity*, 3:673–682, Dec. 1995. Identification and Characterization of a New Member of the TNF Family that induces Apoptosis.
Brian R. Wong, et al., *J. Exp. Med.*, 186(12):2075–2080, Dec. 15, 1997. "TRANCE (Tumor Necrosis Factor [TNF] –related Activation–induced Cytokine), a New TNF Family Member Predominantly Expressed in T cells, Is a Dendritic Cell–specific Survival Factor".
Brian R. Wong, et al., *J. Biological Chemistry*, 272(40):25190–25194, Oct. 3, 1997. "TRANCE Is a Novel Ligand of the Tumor Necrosis factor Receptor Family that Activates c–Jun N–terminal Kinase in T Cells".
M. Goto, et al., *Database WPI*, Section Ch, Week 199850, Derwent Publications Ltd., London, GB; AN 1998–594563 & WO 98 46644 A (Snow Brand Milk Prod Co LTD), Oct. 22, 1998, SEQ ID No. 1, 11, 16, 17 *abstract*.

* cited by examiner

*Primary Examiner*—Phillip Gambel
*Assistant Examiner*—Jessica H. Roark
(74) *Attorney, Agent, or Firm*—Edwin P. Ching; Ping F. Hwung; Andrew Serafini

(57) ABSTRACT

Purified genes encoding a T cell surface antigen from a mammal, reagents related thereto including purified proteins, specific antibodies, and nucleic acids encoding this antigen are provided. Methods of using said reagents and diagnostic kits are also provided.

21 Claims, No Drawings

ANTIBODIES TO MAMMALIAN T CELL SURFACE ANTIGEN

This application is a continuation of U.S. application Ser. No. 08/989,362, filed Dec. 12, 1997, now U.S. Pat. No. 6,242,586, which claims the benefit of U.S. Provisional Application No. 60/032,846, filed on Dec. 13, 1996, the disclosures of which are incorporated by reference.

FIELD OF THE INVENTION

The present invention pertains to compositions related to proteins which function in controlling activation and expansion of mammalian cells, e.g., cells of a mammalian immune system. In particular, it provides purified genes, proteins, antibodies, and related reagents useful, e.g., to regulate activation, development, differentiation, and function of various cell types, including hematopoietic cells.

BACKGROUND OF THE INVENTION

It The activation of resting T cells is critical to most immune responses and allows these cells to exert their regulatory or effector capabilities. See Paul (ed; 1993) *Fundamental Immunolocy* 3d ed., Raven Press, N.Y. Increased adhesion between T cells and antigen presenting cells (APC) or other forms of primary stimuli, e.g., immobilized monoclonal antibodies (mAb), can potentiate the T-cell receptor signals. T-cell activation and T cell expansion depends upon engagement of the T-cell receptor (TCR) and co-stimulatory signals provided by accessory cells. See, e.g., Jenkins and Johnson (1993) *Curr. Opin. Immunol.* 5:361–367; Bierer and Hahn (1993) *Semin. Immunol.* 5:249–261; June, et al. (1990) *Immunol, Today* 11:211–216; and Jenkins (1994) *Immunity* 1:443–446. A major, and well-studied, co-stimulatory interaction for T cells involves either CD28 or CTLA-4 on T cells with either B7 or B70 (Jenkins (1994) *Immunity* 1:443–446). Recent studies on CD28 deficient mice (Shahinian, et al. (1993) *Science* 261:609–612; Green, et al. (1994) *Immunity* 1:501–508) and CTLA-4 immunoglobulin expressing transgenic mice (Ronchese, et al. (1994) *J. Exp. Med.* 179:809–817) have revealed deficiencies in some T-cell responses though these mice have normal primary immune responses and normal CTL responses to lymphocytic choriomeningitis virus and vesicular stomatitis virus. As a result, both these studies conclude that other co-stimulatory molecules must be supporting T-cell function. However, identification of these molecules which mediate distinct costimulatory signals has been difficult.

Tumor Necrosis Factor (TNF) is the prototypic member of an emerging family of cytokines that function as prominent mediators of immune regulation and the inflammatory response. These ligands are typically type II membrane proteins, with homology at the carboxy terminus. A proteolytic processed soluble protein often is produced. See, e.g., Smith, et al. (1994) *Cell* 76–959–962; Armitage (1994) *Current Opinion in Immunolocy* 6:407–413; Gruss and Dower (1995) *Blood* 85:3378–3404; Wiley, et al. (1995) *Immunity* 3:673–682; and Baker and Reddy (1996) *Oncogene* 12:1–9. Crucial roles for these family members are evidenced by a number of studies, and they are implicated in regulation of apoptosis, peripheral tolerance, Ig maturation and isotype switching, and general B cell and T cell functions. See, e.g., Thomson (ed. 1994) *NThe cytokines Handook* Academic Press, San Diego, Calif. These imply fundamental roles in immune and developmental networks.

The inability to modulate activation signals prevents control of inappropriate developmental or physiological responses in the immune system. The present invention provides at least one alternative costimulatory molecule, agonists and antagonists of which will be useful in modulating a plethora of immune responses.

SUMMARY OF THE INVENTION

The present invention is based, in part, upon the discovery of an antigen which exhibits sequence homology to proteins which act as inducers of apoptosis. In particular, it provides a gene encoding a 316 amino acid protein, designated 499E9, which is expressed on a highly polarized Th1 T cell. Engagement of 499E9 may modulate antigen-specific proliferation and cytokine production by effector cells. 499E9 is a novel cell surface molecule which, when engaged, may either potentiate immune cell expansion or apoptosis. The mouse embodiment is described, enabling mammalian genes, proteins, antibodies, and uses thereof. Functional equivalents exhibiting significant sequence homology are available from other mammalian, e.g., human, and non-mammalian species. Moreover, the receptor of 499E9 can function as its binding partner to stimulate other cells expressing the receptor.

More particularly, the present invention provides a composition of matter selected from: a substantially pure or recombinant 499E9 protein or peptide exhibiting at least about 85% sequence identity over a length of at least about 12 amino acids to SEQ ID NO: 2; a natural sequence 499E9 of SEQ ID NO: 2; or a fusion protein comprising 499E9 sequence. Certain embodiments include a substantially pure or isolated protein comprising a segment exhibiting sequence identity to a corresponding portion of a 499E9, wherein: the homology is at least about 90% identity and the portion is at least about 9 amino acids; the homology is at least about 80% identity and the portion is at least about 17 amino acids; or the homology is at least about 70% identity and the portion is at least about 25 amino acids. Other embodiments include a composition of matter, wherein the: 499E9 comprises a mature sequence of Table 1; or protein or peptide: is from a warm blooded animal selected from a mammal, including a rodent; comprises at least one polypeptide segment of SEQ ID NO: 2; exhibits a plurality of portions exhibiting the identity; is a natural allelic variant of 499E9; has a length at least about 30 amino acids; exhibits at least two non-overlapping epitopes which are specific for a mammalian 499E9; exhibits a sequence identity at least about 90% over a length of at least about 20 amino acids to a rodent 499E9; exhibits at least two on-overlapping epitopes which are specific for a rodent 499E9; exhibits a sequence identity at least about 90% over a length of at least about 20 amino acids to a rodent 499E9; is glycosylated; is a synthetic polypeptide; is attached to a solid substrate; is conjugated to another chemical moiety; is a 5-fold or less substitution from natural sequence; or is a deletion or insertion variant from a natural sequence. Also provided are various compositions, e.g., comprising: a sterile 499E9 protein or peptide; or the 499E9 protein or peptide and a carrier, wherein the carrier is: an aqueous compound, including water, saline, and/or buffer; and/or formulated for oral, rectal, nasal, topical, or parenteral administration. Fusion proteins are provided, e.g., comprising: mature protein sequence of Table 1; a detection or purification tag, including a FLAG, His6, or Ig sequence; or sequence of another TNF-ligand protein. Kit embodiments are provided, e.g., comprising such a protein or polypeptide, and: a compartment comprising the protein or polypeptide; and/or instructions for use or disposal of reagents in the kit.

Antibody, or binding compound embodiments include those comprising an antigen binding portion from an antibody, which specifically binds to a natural 499E9 protein, wherein: the protein is a rodent protein; the binding compound is an Fv, Fab, or Fab2 fragment; the binding compound is conjugated to another chemical moiety; or the antibody: is raised against a peptide sequence of a mature polypeptide comprising sequence of Table 1; is raised against a mature 499E9; is raised to a purified 499E9; is immunoselected; is a polyclonal antibody; binds to a denatured 499E9; exhibits a Kd to antigen of at least 30 μM; is attached to a solid substrate, including a bead or plastic membrane; is in a sterile composition; or is detectably labeled, including a radioactive or fluorescent label. Other embodiments include a kit comprising the binding compound, and: a compartment comprising the binding compound; and/or instructions for use or disposal of reagents in the kit. Other forms include, e.g., a composition comprising: a sterile binding compound; or the binding compound and a carrier, wherein the carrier is: an aqueous compound, including water, saline, and/or buffer; and/or formulated for oral, rectal, nasal, topical, or parenteral administration. Such also allow methods of purifying a 499E9 protein or peptide from other materials in a mixture comprising contacting the mixture to such an antibody, and separating bound 499E9 from other materials.

Nucleic acid embodiments include an isolated or recombinant nucleic acid encoding a protein or peptide or fusion protein, wherein: the 499E9 protein is from a mammal, including a rodent; or the nucleic acid: encodes an antigenic peptide sequence of Table 1; encodes a plurality of antigenic peptide sequences of Table 1; exhibits at least about 80% identity to a natural cDNA encoding the segment; is an expression vector; further comprises an origin of replication; is from a natural source; comprises a detectable label; comprises synthetic nucleotide sequence; is less than 6 kb, preferably less than 3 kb; is from a mammal, including a rodent; comprises a natural full length coding sequence; is a hybridization probe for a gene encoding the 499E9 protein; or is a PCR primer, PCR product, or mutagenesis primer. A cell or tissue comprising such a recombinant nucleic acid is also embraced within the invention, e.g., wherein the cell is: a prokaryotic cell; a eukaryotic cell; a bacterial cell; a yeast cell; an insect cell; a mammalian cell; a mouse cell; a rodent cell; or a human cell. Kit forms include those comprising the nucleic acid, and: a compartment comprising the nucleic acid; a compartment further comprising a 499E9 protein or polypeptide; and/or instructions for use or disposal of reagents in the kit. Other nucleic acid embodiments include those which: hybridize under wash conditions of: 30° C. and less than 2M salt, 450° C. and/or 500 mM salt, or at 55° C. and/or 150 mM salt to SEQ ID NO: 1; or exhibit at least about 85% identity over a stretch of at least about 30 nucleotides, at least 90% and/or the stretch is at least 55 nucleotides, or at least 95% and/or the stretch is at least 75 nucleotides to a rodent 499E9.

The invention further provides methods of modulating physiology or development of a cell or tissue culture cells comprising introducing into the cell an agonist or antagonist of a 499E9. Other methods include modulating the physiology of a cell comprising contacting the cell with: a substantially pure 499E9 or fragment; an antibody or binding partner which specifically binds a 499E9; or c) a nucleic acid encoding a 499E9 or peptide. Preferably, the is a T cell and the modulating of physiology is: apoptosis of the T cell; or activation of the T cell.

The invention further provides a method of treating a patient having an abnormal immune response by administering an effective dose of an antibody or binding partner specific for 499E9; a 499E9 protein or polypeptide; or a nucleic acid encoding a 499E9 peptide. The abnormal immune response is characterized by a T cell immune deficiency; chronic inflammation; or tissue rejection.

DETAILED DESCRIPTION OF THE PREFERRED EMBODIMENTS

All references cited herein are incorporated herein by reference to the same extent as if each individual publication or patent application was specifically and individually indicated to be incorporated by reference.

OUTLINE
I. General
II. Purified 499E9
   A. physical properties
   B. biological properties
III. Physical Variants
   A. sequence variants, fragments
   B. post-translational variants
      1. glycosylation
      2. others
IV. Functional Variants
   A. analogs, fragments
      1. agonists
      2. antagonists
   B. mimetics
      1. protein
      2. chemicals
   C. species variants
V. Antibodies
   A. polyclonal
   B. monoclonal
   C. fragments, binding compositions
VI. Nucleic Acids
   A. natural isolates; methods
   B. synthetic genes
   C. methods to isolate
VII. Making 499E9, mimetics
   A. recombinant methods
   B. synthetic methods
   C. natural purification
VIII. Uses
   A. diagnostic
   B. therapeutic
IX. Kits
   A. nucleic acid reagents
   B. protein reagents
   C. antibody reagents
X. Isolating a binding partner (ligand)
I. General The present invention provides amino acid sequences and DNA sequences encoding various mammalian proteins which are antigens found in many T cell subtypes, e.g., Th1, Th2, polarized Th1 cells, and polarized Th2 cells. Among these proteins are antigens which modulate, e.g., induce or prevent proliferation or differentiation of interacting cells, among other physiological effects. The full length antigens, and fragments, or antagonists will be useful in physiological modulation of cells expressing counter receptors for the antigen. The proteins will also be useful as antigens, e.g., immunogens, for raising antibodies to various epitopes on the protein, both linear and conformational epitopes. The molecule may be useful in defining functional T cell or NK cell subsets.

A cDNA encoding 499E9 was isolated from a polarized Th1 cell cDNA library, see Openshaw, et al. (1995) *J. Exp.*

*Med.* 182:1357–1367. The 499E9 cDNA contains a stretch of about 2191 bp in length and contained one large open reading frame encoding a type II transmembrane protein. Transcript analysis has identified multiple transcripts with the most prevalent being 2.1 to 2.3 kb. Structural features include an intracellular domain sequence of about 52 amino acids, an extracellular region of about 246 amino acids, and a hydrophobic presumptive membrane spanning portion of about 20 amino acids. See Table i and SEQ. ID. NO: 2. 499E9 exhibits structural motifs characteristic of a member of the TNF ligand family. Compare, e.g., with the CD40 ligand, OX40 ligand, TNF, NGF, and FAS. Table 1 illustrates the nucleic acid and predicted amino acid sequences for mouse 499E9.

TABLE 1

Mouse 499E9 nucleotide and predicted amino-acid sequence. Predicted intracellular domain sequence runs about from met1 to met49; residues 8 and 11 are potential tyrosine phosphorylation sites; a transmembrane sequence probably runs about from phe50 to leu69; and the extracellular domain probably runs about from tyr70 to asp316. See SEQ ID NO: 1 and 2.

| | |
|---|---|
| GCCAGGACCT CTGTGAACCG GTCGGGGCGG GGGCCGCCTG GCCGGGAGTC TGCTCGGCGG | 60 |
| TGGGTGGCCG AGGAAGGGAG AGAACGATCG CGGAGCAGGG CGCCCGAACT CCGGGCGCCG | 120 |
| CGCC ATG CGC CGG GCC AGC CGA GAC TAC GGC AAG TAC CTG CGC AGC TCG<br>     Met Arg Arg Ala Ser Arg Asp Tyr Gly Lys Tyr Leu Arg Ser Ser<br>      1          5             10              15 | 169 |
| GAG GAG ATG GGC AGC GGC CCC GGC GTC CCA CAC GAG GGT CCG CTG CAC<br>Glu Glu Met Gly Ser Gly Pro Gly Val Pro His Glu Gly Pro Leu His<br>             20              25             30 | 217 |
| CCC GCG CCT TCT GCA CCG GCT CCG GCG CCG CCA CCC GCC GCC TCC CGC<br>Pro Ala Pro Ser Ala Pro Ala Pro Ala Pro Pro Pro Ala Ala Ser Arg<br>             35              40             45 | 265 |
| TCC ATG TTC CTG GCC CTC CTG GGG CTG GGA CTG GGC CAG GTG GTC TGC<br>Ser Met Phe Leu Ala Leu Leu Gly Leu Gly Leu Gly Gln Val Val Cys<br>      50                   55               60 | 313 |
| AGC ATC GCT CTG TTC CTG TAC TTT CGA GCG CAG ATG GAT CCT AAC AGA<br>Ser Ile Ala Leu Phe Leu Tyr Phe Arg Ala Gln Met Asp Pro Asn Arg<br>     65                 70              75 | 361 |
| ATA TCA GAA GAC AGC ACT CAC TGC TTT TAT AGA ATC CTG AGA CTC CAT<br>Ile Ser Glu Asp Ser Thr His Cys Phe Tyr Arg Ile Leu Arg Leu His<br>80                 85               90              95 | 409 |
| GAA AAC GCA GGT TTG CAG GAC TCG ACT CTG GAG AGT GAA GAC ACA CTA<br>Glu Asn Ala Gly Leu Gln Asp Ser Thr Leu Glu Ser Glu Asp Thr Leu<br>            100             105             110 | 457 |
| CCT GAC TCC TGC AGG AGG ATG AAA CAA GCC TTT CAG GGG GCC GTG CAG<br>Pro Asp Ser Cys Arg Arg Met Lys Gln Ala Phe Gln Gly Ala Val Gln<br>           115              120            125 | 505 |
| AAG GAA CTG CAA CAC ATT GTG GGG CCA CAG CGC TTC TCA GGA GCT CCA<br>Lys Glu Leu Gln His Ile Val Gly Pro Gln Arg Phe Ser Gly Ala Pro<br>      130               135             140 | 553 |
| GCT ATG ATG GAA GGC TCA TGG TTG GAT GTG GCC CAG CGA GGC AAG CCT<br>Ala Met Met Glu Gly Ser Trp Leu Asp Val Ala Gln Arg Gly Lys Pro<br>145               150             155 | 601 |
| GAG GCC CAG CCA TTT GCA CAC CTC ACC ATC AAT GCT GCC AGC ATC CCA<br>Glu Ala Gln Pro Phe Ala His Leu Thr Ile Asn Ala Ala Ser Ile Pro<br>160               165             170            175 | 649 |
| TCG GGT TCC CAT AAA GTC ACT CTG TCC TCT TGG TAC CAC GAT CGA GGC<br>Ser Gly Ser His Lys Val Thr Leu Ser Ser Trp Tyr His Asp Arg Gly<br>           180              185            190 | 697 |
| TGG GCC AAG ATC TCT AAC ATG ACG TTA AGC AAC GGA AAA CTA AGG GTT<br>Trp Ala Lys Ile Ser Asn Met Thr Leu Ser Asn Gly Lys Leu Arg Val<br>           195             200             205 | 745 |
| AAC CAA GAT GGC TTC TAT TAC CTG TAC GCC AAC ATT TGC TTT CGG CAT<br>Asn Gln Asp Gly Phe Tyr Tyr Leu Tyr Ala Asn Ile Cys Phe Arg His<br>      210               215             220 | 793 |
| CAT GAA ACA TCG GGA AGC GTA CCT ACA GAC TAT CTT CAG CTG ATG GTG<br>His Glu Thr Ser Gly Ser Val Pro Thr Asp Tyr Leu Gln Leu Met Val | 841 |

TABLE 1-continued

Mouse 499E9 nucleotide and predicted amino-acid sequence.
Predicted intracellular domain sequence runs about from met1 to
met49; residues 8 and 11 are potential tyrosine phosphorylation
sites; a transmembrane sequence probably runs about from phe50 to
leu69; and the extracellular domain probably runs about from tyr70 to
asp316. See SEQ ID NO: 1 and 2.

```
                225                 230                 235
TAT GTC GTT AAA ACC AGC ATC AAA ATC CCA AGT TCT CAT AAC CTG ATG      889
Tyr Val Val Lys Thr Ser Ile Lys Ile Pro Ser His Asn Leu Met
240                 245                 250                 255

AAA GGA GGG AGC ACG AAA AAC TGG TCG GGC AAT TCT GAA TTC CAC TTT      937
Lys Gly Gly Ser Thr Lys Asn Trp Ser Gly Asn Ser Glu Phe His Phe
                260                 265                 270

TAT TCC ATA AAT GTT GGG GGA TTT TTC AAG CTC CGA GCT GGT GAA GAA      985
Tyr Ser Ile Asn Val Gly Gly Phe Phe Lys Leu Arg Ala Gly Glu Glu
                275                 280                 285

ATT AGC ATT CAG GTG TCC AAC CCT TCC CTG CTG GAT CCG GAT CAA GAT     1033
Ile Ser Ile Gln Val Ser Asn Pro Ser Leu Leu Asp Pro Asp Gln Asp
                290                 295                 300

GCG ACG TAC TTT GGG GCT TTC AAA GTT CAG GAC ATA GAC TGAGACTCAT      1082
Ala Thr Tyr Phe Gly Ala Phe Lys Val Gln Asp Ile Asp
                305                 310                 315

TTCGTGGAAC ATTAGCATGG ATGTCCTAGA TGTTTGGAAA CTTCTTAAAA AATGGATGAT   1142

GTCTATACAT GTGTAAGACT ACTAAGAGAC ATGGCCCACG GTGTATGAAA CTCACAGCCC   1202

TCTCTCTTGA GCCTGTACAG GTTGTGTATA TGTAAAGTCC ATAGGTGATG TTAGATTCAT   1262

GGTGATTACA CAACGGTTTT ACAATTTTGT AATGATTTCC TAAGAATTGA ACCAGATTGG   1322

GAGAGGTATT CCGATGCTTA TGAAAAACTT ACACGTGAGC TATGGAAGGG GGTCACAGTC   1382

TCTGGGTCTA ACCCCTGGAC ATGTGCCACT GAGAACCTTG AAATTAAGAA GATGCCATGT   1442

CATTGCAAAG AAATGATAGT GTGAAGGGTT AAGTTCTTTT GAATTGTTAC ATTGCGCTGG   1502

GACCTGCAAA TAAGTTCTTT TTTTCTAATG AGGAGAGAAA AATATATGTA TTTTTATATA   1562

ATGTCTAAAG TTATATTTCA GGTGTAATGT TTTCTGTGCA AAGTTTTGTA AATTATATTT   1622

GTGCTATAGT ATTTGATTCA AAATATTTAA AAATGTCTCA CTGTTGACAT ATTTAATGTT   1682

TTAAATGTAC AGATGTATTT AACTGGTGCA CTTTGTAATT CCCCTGAAGG TACTCGTAGC   1742

TAAGGGGGCA GAATACTGTT TCTGGTGACC ACATGTAGTT TATTTCTTTA TTCTTTTTAA   1802

CTTAATAGAG TCTTCAGACT TGTCAAAACT ATGCAAGCAA AATAAATAAA TAAAAATAAA   1862

ATGAATATCT TGAATAATAA GTAGGATGTT GGTCACCAGG TGCCTTTCAA ATTTAGAAGC   1922

TAATTGACTT TAGGAGCTGA CATAGCCAAA AAGGATACAT AATAGGCTAC TGAAAATCTG   1982

TCAGGAGTAT TTATGCAATT ATTGAACAGG TGTCTTTTTT TACAAGAGCT ACAAATTGTA   2042

AATTTTGTTT CTTTTTTTTC CCATAGAAAA TGTACTATAG TTTATCAGCC AAAAAACAAT   2102

CCACTTTTTA ATTTAGTGAA AGTTATTTTA TTATACTGTA CAATAAAAGC ATTCTTTCTG   2162

AATGGCATTT TTTGGTACTT AAAAATGGC                                    2191
```

TNF ligand family members have a conserved leucine residue corresponding to 205; a conserved glycine residue corresponding to residue 211; a conserved tyrosine residue corresponding to residue 216; a conserved glycine residue corresponding to residue 277; a conserved leucine residue corresponding to residue 282; a conserved phenylalanine residue corresponding to residue 307; and a conserved glycine residue corresponding to residue 308. The TNF ligand domain seems to run about from 205 (leu) to 316 (asp). Glycosylation sites may be at 197 and 262. This clone exhibits closes homology to a mouse TRAIL, which is implicated in induction of apoptosis. Related family members include ligands for CD40 and FAS, and lymphotoxin beta, tumor necrosis factor, etc.

By cDNA Southern analysis, it is clear that 499E9 is expressed in many T cells, including Th1, Th2, 3 week polarized Th1 or Th2 cells, pre T cells, and in Rag knock-out thymus cDNA libraries. Some weak signal from dendritic cells may have been detected. Cells expressing 499E9 typically contain a main transcript of about 2.1 to 2.3 kb, but also containing other transcripts. Tissue distribution analysis suggests a positive signal in brain, heart, kidney, liver, lung, spleen, and testis. Transcripts for 499E9 have not been detected in fibroblasts (L cells), monocytes (RAW264), naive T cells (CD4+, MEL14+, Br cells), macrophage cells, Nippo infected lung/liver/spleen, or Rag knock out organs (brain, heart, kidney, liver, lung, spleen, or testis).

The structural homology of 499E9 to the TNF ligand family suggests function of this molecule. 499E9, as a T cell surface molecule, likely modulates Ag-specific proliferative responses on effector cells, or induction of apoptosis of those cells. 499E9 agonists, or antagonists, may also act as a co-stimulatory molecule for regulation of T cell mediated cell activation, and may in fact, cause a shift of T helper cell types, e.g., between Th1 and Th2. Thus, 499E9 or antagonists should be useful in the treatment of abnormal immune disorders, e.g., T cell immune deficiencies, chronic inflammation, or tissue rejection.

TNF ligand molecules typically modulate cell proliferation, viability, and differentiation. For example, TNF and FAS can kill cells expressing their respective receptors, including fibroblasts, liver cells, and lymphocytes. Some members of this class of ligands exhibit effects on cellular proliferation of cells expressing their respective receptors, e.g., B cells expressing CD40. These effects on proliferation may also effect subsequent differentiation steps, and may lead, directly or indirectly, to changes in cytokine expression profiles.

The members of the TNF ligand family also exhibit costimulation effects, which may also regulate cellular differentiation or apoptosis. Receptor expressing cells may be protected from activation induced cell death (AICD) or apoptosis. For example, CD40 ligand can have effects on T and B lymphocytes.

The embodiment characterized herein is from mouse, but other primate, e.g., human, variants will exist. Additional sequences for proteins in other mammalian species, e.g., primates and rodents, will also be available. See below. The descriptions below are directed, for exemplary purposes, to a mouse 499E9, but are likewise applicable to related embodiments from other species.

The mouse 499E9 protein is a protein which exhibits structural features characteristic of a cell surface antigen, e.g., a TNF ligand family member. The protein is easily detected on particular cell types, others express lesser amounts. The 499E9 antigen should be present in the identified tissue types and the interaction of the antigen with its binding partner should be important for mediating various aspects of cellular physiology or development, as described.

II. Purified 499E9

Mouse 499E9 amino acid sequence is shown in SEQ ID NO: 2. These amino acid sequences, provided amino to carboxy, are important in providing sequence information in the antigen allowing for distinguishing the protein from other proteins and exemplifying numerous variants. Moreover, the peptide sequences allow preparation of peptides to generate antibodies to recognize such segments, and nucleotide sequences allow preparation of oligonucleotide probes, both of which are strategies for detection or isolation, e.g., cloning, of genes or cDNAs encoding such sequences.

As used herein, the term "mouse 499E9" shall encompass, when used in a protein context, a protein having amino acid sequence shown in SEQ ID NO: 2, or a significant fragment of such a protein, or another highly homologous protein derived from mouse. These binding components, e.g., antibodies, typically bind to a 499E9 with high affinity, e.g., at least about 100 nM, usually better than about 30 nM, preferably better than about 10 nM, and more preferably at better than about 3 nM. Homologous proteins would be found in mammalian species other than mouse, e.g., primates or rodents. Non-mammalian species should also possess structurally or functionally related genes and proteins, e.g., birds or amphibians.

The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids.

The term "binding composition" refers to molecules that bind with specificity to 499E9, e.g., in a cell adhesion pairing type fashion, or an antibody-antigen interaction. It also includes compounds, e.g., proteins, which specifically associate with 499E9, including in a natural physiologically relevant protein-protein interaction, either covalent or non-covalent. The molecule may be a polymer, or chemical reagent. A functional analog may be an antigen with structural modifications, or it may be a molecule which has a molecular shape which interacts with the appropriate binding determinants. The compounds may serve as agonists or antagonists of the binding interaction, see, e.g., Goodman, et al. (eds.) (1990) *Goodman & Gilmanls: The Pharmacoloaical Bases of Therapeutics* (8th ed.), Pergamon Press.

Substantially pure typically means that the protein is free from other contaminating proteins, nucleic acids, or other biologicals derived from the original source organism. Purity may be assayed by standard methods, typically by weight, and will ordinarily be at least about 40% pure, generally at least about 50% pure, often at least about 60% pure, typically at least about 80% pure, preferably at least about 90% pure, and in most preferred embodiments, at least about 95% pure. Carriers or excipients will often be added.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. For diagnostic purposes, the temperature will usually be about room temperature or warmer, but less than the denaturation temperature of components in the assay. For therapeutic purposes, the temperature will usually be body temperature, typically about 37° C. for humans and mice, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent and electrolytes will usually be a biologically compatible buffer, of a type used for preservation of biological activities, and will usually approximate a physiological aqueous solvent. Usually the solvent will have a neutral pH, typically between about 5 and 10, and preferably about 7.5. On some occasions, one or more detergents will be added, typically a mild non-denaturing one, e.g., CHS (cholesteryl hemisuccinate) or CHAPS (3-[3-cholamidopropyl)dimethylammonio]-1-propane sulfonate), or a low enough concentration as to avoid significant disruption of structural or physiological properties of the protein.

III. Physical Variants

This invention also encompasses proteins or peptides having substantial amino acid sequence identity with the amino acid sequence of the 499E9. The variants include species, polymorphic, or allelic variants.

Amino acid sequence homology, or sequence identity, is determined by optimizing residue matches, if necessary, by introducing gaps as required. See also Needleham, et al. (1970) *J. Mol. Biol.* 48:443–453; Sankoff, et al. (1983) Chapter One in *Time Warp, String Edits, and Macromolecules: The Theory and Practice of Sequence Comparison*, Addison-Wesley, Reading, Mass.; and software packages from IntelliGenetics, Mountain View, Calif.; and the University of Wisconsin Genetics Computer Group, Madison, Wis. Sequence identity changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural polymorphic or allelic and interspecies variations in each respective protein sequence. Typical homologous proteins or peptides will have from 25–100% identity (if gaps can be introduced), to 50–100% identity (if conservative substitutions are included) with the amino acid sequence of the 499E9. Identity measures will be at least about 35%, generally at least about 40%, often at least about 50%, typically at least about 60%, usually at least about 70%, preferably at least about 80%, and.more preferably at least about 90%.

The isolated 499E9 DNA can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, antigenic, or other functional activity. These modified sequences can be used to produce mutant antigens or to enhance expression. Enhanced expression may involve gene amplification, increased transcription, increased translation, and other mechanisms. "Mutant 499E9" encompasses a polypeptide otherwise falling within the sequence identity definition of the 499E9 as set forth above, but having an amino acid sequence which differs from that of 499E9 as normally found in nature, whether by way of deletion, substitution, or insertion. This generally includes proteins having significant identity with a protein having sequence of SEQ ID NO: 2, and as sharing various biological activities, e.g., antigenic or immunogenic, with those sequences, and in preferred embodiments contain most of the full length disclosed sequences. Full length sequences will typically be preferred, though truncated versions, e.g., soluble constructs and intact domains, will also be useful, likewise, genes or proteins found from natural sources are typically most desired. Similar concepts apply to different 499E9 proteins, particularly those found in various warm blooded animals, e.g., mammals and birds. These descriptions are generally meant to encompass all 499E9 proteins, not limited to the particular mouse embodiments specifically discussed.

499E9 mutagenesis can also be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See, e.g., Sambrook, et al. (1989); Ausubel, et al. (1987 and Supplements); and Kunkel, et al. (1987) *Methods in Enzymol.* 154:367–382.

The present invention also provides recombinant proteins, e.g., heterologous fusion proteins using segments from these proteins. A heterologous fusion protein is a fusion of proteins or segments which are naturally not normally fused in the same manner. A similar concept applies to heterologous nucleic acid sequences. Fusion proteins will be useful as sources for cleaving, separating, and purifying portions thereof.

In addition, new constructs may be made from combining similar functional domains from other proteins. For example, target-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

IV. Functional Variants

The blocking of physiological response to 499E9s may result from the inhibition of binding of the antigen to its binding partner, e.g., another of itself, likely through competitive inhibition. Thus, in vitro assays of the present invention will often use isolated protein, membranes from cells expressing a membrane associated recombinant 499E9, soluble fragments comprising antigen binding segments of these proteins, or fragments attached to solid phase substrates. These assays will also allow for the diagnostic determination of the effects of either binding segment mutations and modifications, or antigen mutations and modifications, e.g., 499E9 analogs.

This invention also contemplates the use of competitive drug screening assays, e.g., where neutralizing antibodies to antigen or binding fragments compete with a test compound for binding to the protein, e.g., of natural protein sequence.

"Derivatives" of 499E9 antigens include amino acid sequence mutants from naturally occurring forms, glycosylation variants, and covalent or aggregate conjugates with other chemical moieties. Covalent derivatives can be prepared by linkage of functionalities to groups which are found in 499E9 amino acid side chains or at the N- or C-termini, e.g., by standard means. See, e.g., Lundblad and Noyes (1988) *Chemical Reagents for Protein Modification*, vols. 1–2, CRC Press, Inc., Boca Raton, Fla.; Hugli (ed.) (1989) *Techniques in Protein Chemistry*, Academic Press, San Diego, Calif.; and Wong (1991) *Chemistry of Protein Conjugation and Cross Linking*, CRC Press, Boca Raton, Fla.

In particular, glycosylation alterations are included, e.g., made by modifying the glycosylation patterns of a polypeptide during its synthesis and processing, or in further processing steps. See, e.g., Elbein (1987) *Ann, Rev. Biochem.* 56:497–534. Also embraced are versions of the peptides with the same primary amino acid sequence which have other minor modifications, including phosphorylated amino acid residues, e.g., phosphotyrosine, phosphoserine, or phosphothreonine.

Fusion polypeptides between 499E9s and other homologous or heterologous proteins are also provided. Many cytokine receptors or other surface proteins are multimeric, e.g., homodimeric entities, and a repeat construct may have various advantages, including lessened susceptibility to proteolytic cleavage. Typical examples are fusions of a reporter polypeptide, e.g., luciferase, with a segment or domain of a protein, e.g., a receptor-binding segment, so that the presence or location of the fused ligand may be easily determined. See, e.g., Dull, et al., U.S. Pat. No. 4,859,609. Other gene fusion partners include bacterial β-galactosidase, trpE, Protein A, β-lactamase, alpha Waylase, alcohol dehydrogenase, yeast alpha mating factor, and detection or purification tags, such as a FLAG sequence of His6 sequence. See, e.g., Godowski, et al. (1988) *Science* 241:812–816.

Fusion peptides will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), vols. 1–3, Cold Spring Harbor Laboratory; and Ausubel, et al. (eds.) (1993) *Current Protocols in Molecular Biology*, Greene and Wiley, N.Y. Techniques for synthesis of polypeptides are described, e.g., in Merrifield (1963) *J. Amer. Chem. Soc.* 85:2149–2156; Merrifield (1986) *Science* 232: 341–347; Atherton, et al. (1989) *Solid Phase Peptide Synthesis: A Practical Approach*, IRL Press, Oxford; and Grant (1992) *Synthetic Pertides: A User's Guide*, W. H. Freeman, N.Y.

This invention also contemplates the use of derivatives of 499E9s other than variations in amino acid sequence or glycosylation. Such derivatives may involve covalent or aggregative association with chemical moieties. Covalent or aggregative derivatives will be useful as immunogens, as reagents in immunoassays, or in purification methods such as for affinity purification of binding partners, e.g., other antigens. A 499E9 can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-499E9 antibodies or an alternative binding composition. The 499E9s can also be labeled with a detectable group, e.g., for use in diagnostic assays. Purification of 499E9 may be effected by an immobilized antibody or complementary binding partner.

A solubilized 499E9 or fragment of this invention can be used as an immunogen for the production of antisera or antibodies specific for binding to the antigen or fragments thereof. Purified antigen can be used to screen monoclonal antibodies or antigen-binding fragments, encompassing antigen binding fragments of natural antibodies, e.g., Fab, Fab', F(ab)2, etc. Purified 499E9s can also be used as a reagent to detect antibodies generated in response to the presence of elevated levels of the antigen or cell fragments containing the antigen, both of which may be diagnostic of an abnormal or specific physiological or disease condition. This invention contemplates antibodies raised against amino acid sequences encoded by nucleotide sequence shown in SEQ ID NO: 1, or fragments of proteins containing it. In particular, this invention contemplates antibodies having binding affinity to or being raised against specific fragments which are predicted to lie outside of the lipid bilayer, both extracellular or intracellular.

The present invention contemplates the isolation of additional closely related species variants. Southern and Northern blot analysis should establish that similar genetic entities exist in other mammals. It is likely that 499E9s are widespread in species variants, e.g., rodents, lagomorphs, carnivores, artiodactyla, perissodactyla, and primates.

The invention also provides means to isolate a group of related antigens displaying both distinctness and similarities in structure, expression, and function. Elucidation of many of the physiological effects of the molecules will be greatly accelerated by the isolation and characterization of additional distinct species variants of them. In particular, the present invention provides useful probes for identifying additional homologous genetic entities in different species.

The isolated genes will allow transformation of cells lacking expression of a corresponding 499E9, e.g., either species types or cells which lack corresponding antigens and exhibit negative background activity. This should allow analysis of the function of 499E9 in comparison to untransformed control cells.

Dissection of critical structural elements which effect the various activation or differentiation functions mediated through these antigens is possible using standard techniques of modern molecular biology, particularly in comparing members of the related class. See, e.g., the homolog-scanning mutagenesis technique described in Cunningham, et al. (1989) *Science* 243:1339–1336; and approaches used in O'Dowd, et al. (1988) *J. Biol Chem.* 263:15985–15992; and Lechleiter, et al. (1990) *EMBO J.* 9:4381–4390.

Intracellular functions would probably involve segments of the antigen which are normally accessible to the cytosol. However, protein internalization may occur under certain circumstances, and interaction between intracellular components and "extracellular" segments may occur. The specific segments of interaction of 499E9 with other intracellular components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolatable by affinity methods or by genetic means, e.g., complementation analysis of mutants.

Further study of the expression and control of 499E9 will be pursued. The controlling elements associated with the antigens should exhibit differential physiological, developmental, tissue specific, or other expression patterns. Upstream or downstream genetic regions, e.g., control elements, are of interest. In particular, physiological or developmental variants, e.g., multiple alternatively processed forms of the antigen have been found. See, e.g., SEQ ID NO: 1. Thus, differential splicing of message may lead to an assortment of membrane bound forms, soluble forms, and modified versions of antigen.

Structural studies of the antigens will lead to design of new antigens, particularly analogs exhibiting agonist or antagonist properties on the molecule. This can be combined with previously described screening methods to isolate antigens exhibiting desired spectra of activities.

V. Antibodies

Antibodies can be raised to various 499E9s, including species, polymorphic, or allelic variants, and fragments thereof, both in their naturally occurring forms and in their recombinant forms. Additionally, antibodies can be raised to 499E9s in either their active forms or in their inactive forms, including native or denatured versions. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective 499E9s, or screened for agonistic or antagonistic activity, e.g., mediated through the antigen or its binding partner. Antibodies may be agnostic or antagonistic, e.g., by sterically blocking ligand binding. These monoclonal antibodies will usually bind with at least a $K_D$ of about 1 mM, more usually at least about 300 $\mu$M, typically at least about 100 $\mu$M, more typically at least about 30 $\mu$M, preferably at least about 10 $\mu$M, and more preferably at least about 3 $\mu$M or better.

The antibodies of this invention can also be useful in diagnostic applications. As capture or non-neutralizing antibodies, they can be screened for ability to bind to the antigens without inhibiting binding by a partner. As neutralizing antibodies, they can be useful in competitive binding assays. They will also be useful in detecting or quantifying 499E9 protein or its binding partners. See, e.g., Chan (ed.) (1987) *Immunology: A Practical Guide*, Academic Press, Orlando, Fla.; Price and Newman (eds.) (1991) *Principles and Practice of Immunoassay*, Stockton Press, N.Y.; and Ngo (ed.) (1988) *Nonisotopic Immunoassay*, Plenum Press, N.Y. Cross absorptions or other tests will identify antibodies which exhibit various spectra of specificities, e.g., unique or shared species specificities.

Further, the antibodies, including antigen binding fragments, of this invention can be potent antagonists that bind to the antigen and inhibit functional binding or inhibit the ability of a binding partner to elicit a biological response. They also can be useful as non-neutralizing antibodies and can be coupled to toxins or radionuclides so that when the antibody binds to antigen, a cell expressing it, e.g., on its surface, is killed. Further, these antibodies can be conjugated to drugs or other therapeutic agents, either directly or indirectly by means of a linker, and may effect drug targeting.

Antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; Williams, et al. (1967) *Methods in Immunology and Immunochemistry*, vol. 1, Academic Press, New York; and Harlow and Lane (1988) *Antibodies: A Laboratory Manual*, CSH Press, N.Y., for descriptions of methods of preparing polyclonal antisera.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Princitles and Practice* (2d ed.), Academic Press, New York; and particularly in Kohler and Milstein (1975) in *Nature* 256:495–497, which discusses one method of generating monoclonal antibodies.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; Moore, et al., U.S. Pat. No. 4,642,334; and Queen, et al. (1989) *Proc. Nat'l Acad. Sci. USA* 86:10029–10033.

The antibodies of this invention can also be used for affinity chromatography in isolating the protein. Columns can be prepared where the antibodies are linked to a solid support. See, e.g., Wilchek et al. (1984) *Meth. Enzymol.* 104:3–55.

Antibodies raised against each 499E9 will also be useful to raise anti-idiotypic antibodies. These will be useful in detecting or diagnosing various immunological conditions related to expression of the respective antigens.

VI. Nucleic Acids

The described peptide sequences and the related reagents are useful in detecting, isolating, or identifying a DNA clone encoding 499E9, e.g., from a natural source. Typically, it will be useful in isolating a gene from mammal, and similar procedures will be applied to isolate genes from other species, e.g., warm blooded animals, such as birds and mammals. Cross hybridization will allow isolation of 499E9 from other species. A number of different approaches should be available to successfully isolate a suitable nucleic acid clone.

The purified protein or defined peptides are useful for generating antibodies by standard methods, as described above. Synthetic peptides or purified protein can be presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual*, Cold Spring Harbor Press. Alternatively, the 499E9 can be used as a specific binding reagent, and advantage can be taken of its specificity of binding, much like an antibody would be used.

For example, the specific binding composition could be used for screening of an expression library made from a cell line which expresses a 499E9. The screening can be standard staining of surface expressed antigen, or by panning. Screening of intracellular expression can also be performed by various staining or immunofluorescence procedures. The binding Compositions could be used to affinity purify or sort out cells expressing the protein.

The peptide segments can also be used to predict appropriate oligonucleotides to screen a library. The genetic code can be used to select appropriate oligonucleotides useful as probes for screening. See, e.g., SEQ ID NO: 1. In combination with polymerase chain reaction (PCR) techniques, synthetic oligonucleotides will be useful in selecting correct clones from a library. Complementary sequences will also be used as probes, primers, or antisense strands. Based upon identification of the likely extracellular domain, various fragments should be particularly useful, e.g., coupled with anchored vector or poly-A complementary PCR techniques or with complementary DNA of other peptides.

This invention contemplates use of isolated DNA or fragments to encode a biologically active corresponding 499E9 polypeptide. In addition, this invention covers isolated or recombinant DNA which encodes a biologically active protein or polypeptide which is capable of hybridizing under appropriate conditions with the DNA sequences described herein. Said biologically active protein or polypeptide can be an intact antigen, or fragment, and have an amino acid sequence disclosed in, e.g., SEQ ID NO: 1. Further, this invention covers the use of isolated or recombinant DNA, or fragments thereof, which encode proteins which are homologous to a 499E9 or which was isolated using cDNA encoding a 499E9 as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and/or flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Generally, the nucleic acid will be in a vector or fragment less than about 50 kb, usually less than about 30 kb, typically less than about 10 kb, and preferably less than about 6 kb.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, e.g., products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site.

Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least about 22 nucleotides, ordinarily at least about 29 nucleotides, more often at least about 35 nucleotides, typically at least about 41 nucleotides, usually at least about 47 nucleotides, preferably at least about 55 nucleotides, and in particularly preferred embodiments will be at least about 60 or more nucleotides.

A DNA which codes for a 499E9 protein will be particularly useful to identify genes, mRNA, and cDNA species which code for related or homologous proteins, as well as DNAs which code for homologous proteins from different species. There are likely homologs in other species, including primates, rodents, and birds. Various 499E9 proteins should be homologous and are encompassed herein. However, even genes encoding proteins that have a more distant evolutionary relationship to the antigen can readily be isolated under appropriate conditions using these sequences if they are sufficiently homologous. Primate 499E9 proteins are of particular interest.

Recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology*, Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987)(ed.) *Teratocarcinomas and Etbryonic Stem Cells: A Practical Approach*, IRL Press, Oxford; and Rosenberg (1992) *J. Clinical Oncology* 10:180–199

Substantial homology in the nucleic acid sequence comparison context means either that the segments, or their complementary strands, when compared, are identical when optimally aligned, with appropriate nucleotide insertions or deletions, in at least about 50% of the nucleotides, generally at least about 58%, ordinarily at least about 65%, often at least about 71%, typically at least about 77%, usually at least about 85%, preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence of 499E9, e.g., in SEQ ID NO: 1. Typically, selective hybridization will occur when there is at least about 55% homology over a stretch of at least about 30 nucleotides, preferably at least about 75% over a stretch of about 25 nucleotides, and most preferably at least about 90% over about 20 nucleotides. See, Kanehisa (1984) *Nuc. Acids Res.* 12:203–213. The length of homology comparison, as described, may be over longer stretches, and in certain embodiments will be over a stretch of at least about 17 nucleotides, usually at least about 28 nucleotides, typically at least about 40 nucleotides, and preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., usually in excess of about 37° C., typically in excess of about 55° C., preferably in excess of about 70° C. Stringent salt conditions will ordinarily be less than about 1000 mM, usually less than about 400 mM, typically less than about 250 mM, preferably less than about 150 mM. However, the combination of parameters is much more important than the measure of any single parameter. See, e.g., Wetmur and Davidson (1968) *J. Mol. Biol.* 31:349–370.

499E9 from other mammalian species can be cloned and isolated by cross-species hybridization of closely related species. Homology may be relatively low between distantly related species, and thus hybridization of relatively closely related species is advisable. Alternatively, preparation of an antibody preparation which exhibits less species specificity may be useful in expression cloning approaches.

VII. Making 499E9; Mimetics

DNA which encodes the 499E9 or fragments thereof can be obtained by chemical synthesis, screening cDNA libraries, or screening genomic libraries prepared from a wide variety of cell lines or tissue samples. See, e.g., Okayama and Berg (1982) *Mol. Cell. Biol.* 2:161–170; Gubler and Hoffman (1983) *Gene* 25:263–269; and Glover (ed.) (1984) *DNA Clonina: A Practical Approach*, IRL Press, Oxford. Alternatively, the sequences provided herein provide useful PCR primers or allow synthetic or other preparation of suitable genes encoding a 499E9; including, naturally occurring embodiments.

This DNA can be expressed in a wide variety of host cells for the synthesis of a full-length 499E9 or fragments which can in turn, e.g., be used to generate polyclonal or monoclonal antibodies; for binding studies; for construction and expression of modified molecules; and for structure/function studies.

Vectors, as used herein, comprise plasmids, viruses, bacteriophage, integratable DNA fragments, and other vehicles which enable the integration of DNA fragments into the genome of the host. See, e.g., Pouwels, et al. (1985 and Supplements) *Cloning Vectors: A Laboratory Manual*, Elsevier, N.Y.; and Rodriguez, et al. (1988)(eds.) *Vectors; A Survey of Molecular Cloning Vectors and Their Uses*, Buttersworth, Boston, Mass.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression. See e.g., Rodriguez, et al., Chapter 10, pp. 205–236; Balbas and Bolivar (1990) *Methods in Enzymology* 185:14–37; and Ausubel, et al. (1993) *Current Protocols in Molecular Biology*, Greene and Wiley, NY.

Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610. See, e.g., Miller (1988) *Ann. Rev. Microbiol.* 42:177–199.

It will often be desired to express a 499E9 polypeptide in a system which provides a specific or defined glycosylation pattern. See, e.g., Luckow and Summers (1988) *Bio/Technology* 6:47–55; and Kaufman (1990) *Meth. Enzymol.* 185:487–511.

The 499E9, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

Now that the 499E9 has been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Pentide Synthesis*, Springer-Verlag, New York; Bodanszky (1984) *The Principles of Peotide Synthesis*, Springer-Verlag, New York; and Villafranca (ed.) (1991) *Techniques in Protein Chemistry II*, Academic Press, San Diego, Calif.

VIII. Uses

The present invention provides reagents which will find use in diagnostic applications as described elsewhere herein, e.g., in the general description for T cell mediated conditions, or below in the description of kits for diagnosis.

This invention also provides reagents with significant therapeutic value. The 499E9 (naturally occurring or recombinant), fragments thereof, and antibodies thereto, along with compounds identified as having binding affinity to 499E9, should be useful in the treatment of conditions associated with abnormal physiology or development, including abnormal proliferation, e.g., cancerous conditions, or degenerative conditions. In particular, modulation of development of lymphoid cells will be achieved by appropriate therapeutic treatment using the compositions provided herein. For example, a disease or disorder associated with abnormal expression or abnormal signaling by a 499E9 should be a likely target for an agonist or antagonist of the antigen. The antigen plays a role in regulation or development of hematopoietic cells, e.g., lymphoid cells, which affect immunological responses, e.g., autoimmune disorders.

In particular, the antigen will likely provide a costimulatory signal to cell activation. Thus, the 499E9 will likely modulate T cell mediated interactions with other cell types, e.g., cells which possess a receptor therefor. These interactions would lead, in particular contexts, to modulation of cell growth, cytokine synthesis by those or other cells, or development of particular effector cells.

Moreover, the 499E9 or antagonists could redirect T cell responses, e.g., between Th1 and Th2 polarization, or with Th0 cells. Among these agonists should be various antibodies which recognize the appropriate epitopes, e.g., which mimic binding of 499E9 to its receptor. Alternatively, they may bind to epitopes which sterically can block receptor binding.

Antagonists of 499E9, such as the naturally occurring secreted form of 499E9 or blocking antibodies, may also be useful, They may provide a selective and powerful way to modulate immune responses in abnormal situations, e.g., autoimmune disorders, including rheumatoid arthritis, systemic lupus erythematosis (SLE), Hashimoto's autoimmune thyroiditis, as well as acute and chronic inflammatory ,responses in which T cell activation, expansion, and/or immunological T cell memory play an important role. See also Samter, et al. (eds) *Immunological Diseases* vols. 1 and 2, Little, Brown and Co. Regulation of T cell activation, expansion, and/or cytokine release by the naturally occurring secreted form of 499E9, or an antagonist thereof, may be effected.

In addition, certain combination compositions with other modulators of T cell signaling would be useful. Such other signaling molecules include TcR reagents, CD40, CD40L, CTLA-8, CD28, SLAM, FAS, and their respective antagonists.

Various abnormal conditions are known in each of the cell types shown to possess 499E9 mRNA by Northern blot analysis. See Berkow (ed.) *The Merck Manual of Diagnosis and Therapy*, Merck & Co., Rahway, N.J.; Thorn, et al. *Harrison's Principles of Internal Medicine*, McGraw-Hill, N.Y.; and Weatherall, et al. (eds.) *Oxford Textbook of Medicine*, Oxford University Press, Oxford. Many other medical conditions and diseases involve T cells or are T cell mediated, and many of these will be responsive to treatment by an agonist or antagonist provided herein. See, e.g., Stites and Terr (eds; 1991) *Basic and Clinical Immunology*Appleton and Lange, Norwalk, Conn.; and Samter, et al. (eds) *Immunological Diseases* Little, Brown and Co. These problems should be susceptible to prevention or treatment using compositions provided herein.

499E9 antibodies can be purified and then administered to a patient, veterinary or human. These reagents can be combined for therapeutic use with additional active or inert ingredients, e.g., in conventional pharmaceutically acceptable carriers or diluents, e.g., immunogenic adjuvants, along with physiologically innocuous stabilizers, excipients, or preservatives. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using 499E9 or fragments thereof can be performed to identify compounds having binding affinity to or other relevant biological effects on 499E9 functions, including isolation of associated components. Subsequent biological assays can then be utilized to determine if the compound has intrinsic stimulating activity or is a blocker or antagonist in that it blocks the activity of the antigen, e.g., mutein antagonists. Likewise, a compound having intrinsic stimulating activity can activate the signal pathway and is thus an agonist in that it simulates the activity of 499E9. This invention further contemplates the therapeutic use of blocking antibodies to 499E9 as antagonists and of stimulatory molecules, e.g., muteins, as agonists. This approach should be particularly useful with other 499E9 species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilmans: The Pharmacological Bases of Therapeutics*, 8th Ed., Pergamon Press; and *Remington's Pharmaceutical Sciences*, 17th ed. (1990), Mack Publishing Co., Easton, Penn. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 $\mu$M (picomolar), and most preferably less than about 1 fM (femtomolar), with an appropriate carrier. Slow release formulations, or a slow release apparatus will often be utilized for continuous or long term administration. See, e.g., Langer (1990) *Science* 249:1527–1533.

499E9, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, topical, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; Avis, et al. (eds.) (1993) *Pharmaceutical Dosaae Forms: Parenteral Medications*, Dekker, New York.; Lieberman, et al. (eds.) (1990) *Pharmaceutical Dosaae Forms: Tablets*, Dekker, New York; and Lieberman, et al. (eds.) (1990) *Pharmaceutical Dosaae Forms: Disperse Systems*, Dekker, New York. The therapy of this invention may be combined with or used in association with other agents, e.g., other modulators of T cell activation, e.g., CD40, CD40 ligand, CD28, CTLA-4, B7, B70, SLAM, T cell receptor signaling entities, or their respective antagonists.

Both the naturally occurring and the recombinant form of the 499E9s of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate. The development of suitable assays can be greatly facilitated by the availability of large amounts of purified, soluble 499E9 as provided by this invention.

Other methods can be used to determine the critical residues in the 499E9–499E9 receptor interactions. Mutational analysis can be performed, e.g., see Somoza, et al. (1993) *J. Exptl. Med.* 178:549–558, to determine specific residues critical in the interaction and/or signaling. Both extracellular domains, involved in the homophilic interaction, or intracellular domain, which provides interactions important in intracellular signaling.

For example, antagonists can normally be found once the antigen has been structurally defined, e.g., by tertiary structure data. Testing of potential interacting analogs is now possible upon the development of highly automated assay methods using a purified 499E9. In particular, new agonists and antagonists will be discovered by using screening techniques described herein. Of particular importance are compounds found to have a combined binding affinity for a spectrum of 499E9 molecules, e.g., compounds which can serve as antagonists for species variants of 499E9.

One method of drug screening utilizes eukaryotic or prokaryotic host cells which are stably transformed with recombinant DNA molecules expressing a 499E9. Cells may be isolated which express a 499E9 in isolation from other molecules. Such cells, either in viable or fixed form, can be used for standard binding partner binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses.

Another technique for drug screening involves an approach which provides high throughput screening for compounds having suitable binding affinity to a 499E9 and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified 499E9, and washed. The next step involves detecting bound 499E9.

Rational drug design may also be based upon structural studies of the molecular shapes of the 499E9 and other effectors or analogs. Effectors may be other proteins which mediate other functions in response to binding, or other proteins which normally interact with 499E9. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York.

IX. Kits

This invention also contemplates use of 499E9 proteins, fragments thereof, peptides, and their fusion products in a variety of diagnostic kits and methods for detecting the presence of another 499E9 or binding partner. Typically the kit will have a compartment containing either a defined 499E9 peptide or gene segment or a reagent which recognizes one or the other, e.g., 499E9 fragments or antibodies.

A kit for determining the binding affinity of a test compound to a 499E9 would typically comprise a test compound; a labeled compound, for example a binding partner or antibody having known binding affinity for 499E9; a source of 499E9 (naturally occurring or recombinant); and a means for separating bound from free labeled compound, such as a solid phase for immobilizing the molecule. Once compounds are screened, those having suitable binding affinity to the antigen can be evaluated in suitable biological assays, as are well known in the art, to determine whether they act as agonists or antagonists to the 499E9 signaling pathway. The availability of recombinant 499E9 polypeptides also provide well defined standards for calibrating such assays.

A preferred kit for determining the concentration of, e.g., a 499E9 in a sample would typically comprise a labeled compound, e.g., binding partner or antibody, having known binding affinity for the antigen, a source of antigen !(naturally occurring or recombinant) and a means for separating the bound from free labeled compound, e.g., a solid phase for immobilizing the 499E9. Compartments containing reagents, and instructions, will normally be provided.

Antibodies, including antigen binding fragments, specific for the 499E9 or fragments are useful in diagnostic applications to detect the presence of elevated levels of 499E9 and/or its fragments. Such diagnostic assays can employ lysates, live cells, fixed cells, immunofluorescence, cell cultures, body fluids, and further can involve the detection of antigens related to the antigen in serum, or the like. Diagnostic assays may be homogeneous (without a separation step between free reagent and antigen-binding partner complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. See, e.g., Van Vunakis, et al. (1980) *Meth Enzymol.* 70:1–525; Harlow and Lane (1980) *Antibodies: A Laboratory Manual*, CSH Press, NY; and Coligan, et al. (eds.) (1993) *Current Protocols in Immunology*, Greene and Wiley, NY.

Anti-idiotypic antibodies may have similar use to diagnose presence of antibodies against a 499E9, as such may be diagnostic of various abnormal states. For example, overproduction of 499E9 may result in production of various immunological reactions which may be diagnostic of abnormal physiological states, particularly in proliferative cell conditions such as cancer or abnormal activation or differentiation.

Frequently, the reagents for diagnostic assays are supplied in kits, so as to optimize the sensitivity of the assay. For the subject invention, depending upon the nature of the assay, the protocol, and the label, either labeled or unlabeled antibody or binding partner, or labeled 499E9 is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the binding partner, test compound, 499E9, or antibodies thereto can be labeled either directly or indirectly. Possibilities for direct labeling include label groups: radiolabels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free 499E9, or alternatively the bound from the free test compound. The 499E9 can be immobilized on various matrixes followed by washing. Suitable matrixes include plastic such as an ELISA plate, filters, and beads. See, e.g., Coligan, et al. (eds.) (1993) *Current Protocols in Immunology*, Vol. 1, Chapter 2, Greene and Wiley, NY. Other suitable separation techniques include, without limitation, the fluorescein antibody magnetizable particle method described in Rattle, et al. (1984) *Clin. Chem.*

30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a 499E9. These sequences can be used as probes for detecting levels of the 499E9 message in samples from patients suspected of having an abnormal condition, e.g., cancer or developmental problem. Since the antigen is a marker for activation, it may be useful to determine the numbers of activated T cells to determine, e.g., when additional suppression may be called for. The preparation of both RNA and DNA nucleotide sequences, the labeling of the sequences, and the preferred size of the sequences has received ample description and discussion in the literature. See, e.g., Langer-Safer, et al. (1982) *Proc. Nat'l. Acad. Sci.* 79:4381–4385; Caskey (1987) *Science* 236:962–967; and Wilchek et al. (1988) *Anal. Biochem.* 171:1–32.

Diagnostic kits which also test for the qualitative or quantitative presence of other markers are also contemplated. Diagnosis or-prognosis may depend on the combination of multiple indications used as markers. Thus, kits may test for combinations of markers. See, e.g., Viallet, et al. (1989) *Progress in Growth Factor Res.* 1:89–97. Other kits may be used to evaluate T cell subsets.

X. Methods for Isolating 499E9 Specific Binding Partners

The 499E9 protein should interact with a receptor based, e.g., upon its similarity in structure and function to other cell surface antigens exhibiting similar structure and cell type specificity of expression. Methods to isolate a receptor are made available by the ability to make purified 499E9 for screening programs. Soluble or other constructs using the 499E9 sequences provided herein will allow for screening or isolation of 499E9 specific receptors. Many methods exist for expression cloning, panning, affinity isolation, or other means to identify a receptor.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

EXAMPLES

General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual* (2d ed.), vols. 1–3, CSH Press, N.Y.; Ausubel, et al., *Biology*, Greene Publishing Associates, Brooklyn, N.Y.; or Ausubel, et al. (1987 and Supplements) *Current Protocols in Molecular Biology*, Greene and Wiley, New York; Innis, et al. (eds.) (1990) *PCR Protocols: A Guide to Methods and Applications*, Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "purification of Recombinant Proteins with Metal Chelate Absorbent" in Setlow (ed.) *Genetic Engineering, Principle and Methods* 12:87–98, Plenum Press, N.Y.; and Crowe, et al. (1992) *OIAexoress: The High Level Expression & Protein Purification System* QUIAGEN, Inc., Chatsworth, Calif. Cell culture techniques are described in Doyle, et al. (eds.) (1994) *Cell and Tissue Culture: Laboratory Procedures*, John Wiley and Sons, NY.

FACS analyses are described in Melamed, et al. (1990) *Flow Cyctometry and Sorting* Wiley-Liss, Inc., New York, N.Y.; Shapiro (1988) *Practical Flow Cyctometry* Liss, New York, N.Y.; and Robinson, et al. (1993) *Handbook of Flow Cytometry Methods* Wiley-Liss, New York, N.Y. Fluorescent labeling of appropriate reagents was performed by standard methods.

Example 1

Cloning of Mouse 499E9

Production of 3W Th1 or Th2 cells is described in Openshaw, et al. (1995) *J. Exp. Med.* 182:1357–1367. Briefly, Th1 or Th2 populations were derived from CD4+ T cells stimulated with antigen and antigen presenting cells in the presence of IL-12 or IL-4. Cells were stimulated once each week for 3 weeks, then harvested and restimulated, e.g., with PMA and ionomycin for 4 h. See Murphy, et al. (1996) *J. Exp. Med.* 183:901–913.

Total RNA can be isolated, e.g., using the guanidine thiocyanate/CsCl gradient procedure as described by Chirgwin, et al. (1978) *Biochem.* 18:5294–5299. Poly(A)+ RNA is isolated using, e.g., the OLIGOTEX mRNA isolation kit (QIAGEN). Such RNA from these cells is used to synthesize first strand cDNA, e.g., by using NotI/Oligo-dT primer (Gibco-BRL, Gaithersburg, Md.). Double-stranded cDNA is synthesized, ligated with BstXI adaptors, digested with NotI, size fractionated for >0.5 kilobase pairs (kb) and ligated into the NotI/BstXI sites of pJFE-14, a derivative of the pCDSRα vector. See Takebe, et al. (1985) *Mol. Cell Biol.* 8:466–472. Electro-competent *E. coli* DH10α cells (Gibco-BRL) are used for transformation.

Independent clones were randomly picked and screened by hybridization using a cocktail of known cytokine cDNA's. Plasmid DNA's were prepared from clones that did not hybridize to the cytokine probes. These clones were grouped by insert size and further characterized by DNA sequencing. Clones corresponding to the 499E9 were isolated.

Example 2

Cellular Expression of Mouse 499E9

A probe specific for cDNA encoding mouse 499E9 is used to determine tissue distribution of message encoding the antigen. Standard hybridization probes may be used to do a Northern analysis of RNA from appropriate sources, either cells, e.g., stimulated or in various physiological states, in various tissues, e.g., spleen, liver, thymus, lung, etc., or in various species. Southern analysis of cDNA libraries may also provide valuable distribution information. Standard tissue blots or species blots are commercially available. Similar techniques will be useful for evaluating diagnostic or medical conditions which may correlate with expression in various cell types.

PCR analysis using appropriate primers may also be used. Antibody analysis, including immunohistochemistry or FACS, may be used to determine cellular or tissue distribution.

Example 3

Purification of 499E9 Protein

Multiple transfected cell lines are screened for one which expresses the antigen, membrane bound or soluble forms, at a high level compared with other cells. Various cell lines are screened and selected for their favorable properties in handling. Natural 499E9 can be isolated from natural sources, or by expression from a transformed cell using an appropriate expression vector. Purification of the expressed protein is achieved by standard procedures, or may be combined with engineered means for effective purification at high efficiency from cell lysates or supernatants. FLAG or $His_6$ segments can be used for such purification features.

Example 4

Isolation of Homologous 499E9 Genes

The 499E9 cDNA can be used as a hybridization probe to screen a library from a desired source, e.g., a primate cell cDNA library. Many different species can be screened both for stringency necessary for easy hybridization, and for presence using a probe. Appropriate hybridization conditions will be used to select for clones exhibiting specificity of cross hybridization.

Screening by hybridization or PCR using degenerate probes based upon the peptide sequences will also allow isolation of appropriate clones. Alternatively, use of appropriate primers for PCR screening will yield enrichment of appropriate nucleic acid clones.

Similar methods are applicable to isolate either species, polymorphic, or allelic variants. Species variants are isolated using cross-species hybridization techniques based upon isolation of a full length isolate or fragment from one species as a probe.

Alternatively, antibodies raised against mouse 499E9 will be used to screen for cells which express cross-reactive proteins from an appropriate, e.g., cDNA library. The purified protein or defined peptides are useful for generating antibodies by standard methods, as described above. Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. The resulting antibodies are used, e.g., for screening, panning, or sorting.

Example 5

Preparation of Antibodies Specific for 499E9

Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. Polyclonal serum, or hybridomas may be prepared. In appropriate situations, the binding reagent is either labeled as described above, e.g., fluorescence or otherwise, or immobilized to a substrate for panning methods.

Example 6

Isolation of a Receptor for 499E9

A 499E9 construct expression product can be used as a specific binding reagent to identify its binding partner, e.g., receptor, by taking advantage of its specificity of binding, much like an antibody would be used. A 499E9 reagent is either labeled as described above, e.g., fluorescence or otherwise, or immobilized to a substrate for panning methods.

The binding composition is used to screen an expression library made from a cell line which expresses a binding partner, i.e. receptor. Standard staining techniques are used to detect or sort intracellular or surface expressed receptor, or surface expressing transformed cells are screened by panning. Screening of intracellular expression is performed by various staining or immunofluorescence procedures. See also McMahan, et al. (1991) *EMBO J*. 10:2821–2832.

Alternatively, 499E9 reagents are used to affinity purify or sort out cells expressing a receptor. See, e.g., Sambrook, et al. or Ausubel, et al.

Another strategy is to screen for a membrane bound receptor by panning. The cDNA containing receptor cDNA is constructed as described above. The ligand can be immobilized and used to immobilize expressing cells. Immobilization may be achieved by use of appropriate antibodies which recognize, e.g., a FLAG sequence of a 499E9 fusion construct, or by use of antibodies raised against the first antibodies. Recursive cycles of selection and amplification lead to enrichment of appropriate clones and eventual isolation of receptor expressing clones.

Phage expression libraries can be screened by 499E9. Appropriate label techniques, e.g., anti-FLAG antibodies, will allow specific labeling of appropriate clones.

Further studies have been performed by others, which support the scope and breadth of the present disclosure and invention. Two reports have appeared since the date of Applicants' priority filing. See, e.g., Wong, et al. (1997) *J. Biol. Chem*. 272:2510–25194; and Anderson, et al. (1997) *Nature* 390:175–179. These reports verify that other mammalian counterparts do exist, and that a receptor for the ligand also exists. Moreover, they establish significant biology for the genes, as described.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled.

What is claimed is:

1. An isolated antibody, or antigen binding fragment thereof, that specifically binds to a 499E9 polypeptide having the amino acid sequence as shown in SEQ ID NO: 2.

2. The antibody or antigen binding fragment of claim 1, wherein the antibody is polyclonal.

3. The antibody or antigen binding fragment of claim 1, wherein the antibody is monoclonal.

4. The antibody or antigen binding fragment of claim 1, wherein them antibody is a 499E9 antagonist.

5. The antibody or antigen binding fragment of claim 4, wherein the antigen binding fragment is a F(ab')$_2$, Fab, or F$_v$ fragment.

6. The antibody of claim 1, wherein the antibody binds to a 499E9 polypeptide with a K$_d$ of at least about 30 μM.

7. The antibody of claim 1, wherein the antibody binds to a 499E9 polypeptide with a K$_d$ of at least about 10 μM.

8. The antibody of claim 1, or antigen binding fragment thereof, that is raised against a polypeptide selected from the group consisting of:
   a) a substantially pure or recombinant 499E9 polypeptide exhibiting 100% sequence identity over a length of at least 12 contiguous amino acids to SEQ ID NO: 2;
   b) a natural sequence 499E9 of SEQ ID NO:2; and
   c) a fusion protein comprising 499E9 sequence.

9. The antibody of claim 1, wherein the antibody binds to a 499E9 polypeptide with a K$_d$ of at least about 3 μM.

10. An isolated antibody, or antigen binding fragment thereof, that specifically binds to a polypeptide having the amino acid sequence as shown in SEQ ID NO: 2, wherein the antibody or antigen binding fragment is conjugated to a detectable label.

11. The antibody or antigen binding fragment of claim 10, wherein the detectable label is an enzyme, a fluorescent label, or radioisotope.

12. An isolated antibody, or antigen binding fragment thereof, that binds to the polypeptide of SEQ ID NO:2.

13. The antibody or antigen binding fragment of claim 8, wherein the antibody is polyclonal.

14. The antibody or antigen binding fragment of claim 8, wherein the antibody is monoclonal.

15. The antibody or antigen binding fragment of claim 8, wherein the antibody is a 499E9 antagonist.

16. The antibody or antigen binding fragment of claim 8, wherein the antigen binding fragment is a F(ab')$_2$, Fab, or F$_v$ fragment.

17. The antibody or antigen binding fragment of claim 8, wherein the antibody or fragment binds to the polypeptide with a K$_d$ of at least about 30 $\mu$M.

18. The antibody or antigen binding fragment of claim 8, wherein the antibody or fragment binds to the polypeptide with a K$_d$ of at least about 10 $\mu$M.

19. The antibody or antigen binding fragment of claim 8, wherein the antibody or fragment binds to the polypeptide with a K$_d$ of at least about 3 $\mu$M.

20. An isolated antibody, or antigen binding fragment thereof, that specifically binds to a 499E9 polypeptide having the amino acid sequence as shown in SEQ ID NO: 2, wherein the antibody is raised against a polypeptide selected from the group consisting of:

a) a substantially pure or recombinant 499E9 polypeptide exhibiting 100% sequence identity over a length of at least 12 contiguous amino acids to SEQ ID NO: 2;

b) a natural sequence 499E9 of SEQ ID NO:2; and c) a fusion protein comprising 499E9 sequence;

wherein the antibody or antigen binding fragment is conjugated to a detectable label.

21. The antibody or antigen binding fragment of claim 20, wherein the detectable label is an enzyme, a fluorescent label, or radioisotope.

* * * * *

UNITED STATES PATENT AND TRADEMARK OFFICE
CERTIFICATE OF CORRECTION

PATENT NO.   : 6,525,180 B1
DATED        : February 25, 2003
INVENTOR(S)  : Gorman et al.

It is certified that error appears in the above-identified patent and that said Letters Patent is hereby corrected as shown below:

Column 33,
Line 62, please delete "them" and replace it with -- the --.

Signed and Sealed this

Fifteenth Day of April, 2003

JAMES E. ROGAN
*Director of the United States Patent and Trademark Office*

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
       (A) LENGTH: 2191 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 125..1072

(xi) SEQUENCE DESCRIPTION: SEQ ID NO: 1:

```
GCCAGGACCT CTGTGAACCG GTCGGGGCGG GGGCCGCCTG GCCGGGAGTC TGCTCGGCGG        60

TGGGTGGCCA AGGAAGGGAG AGAACGATCG CGGAGCAGGG CGCCCGAACT CCGGGCGCCG       120

CGCC ATG CGC CGG GCC AGC CGA GAC TAC GGC AAG TAC CTG CGC AGC TCG       169
     Met Arg Arg Ala Ser Arg Asp Tyr Gly Lys Tyr Leu Arg Ser Ser
      1               5                  10                  15

GAG GAG ATG GGC AGC GGC CCC GGC GTC CCA CAC GAG GGT CCG CTG CAC        217
Glu Glu Met Gly Ser Gly Pro Gly Val Pro His Glu Gly Pro Leu His
 20              25                  30

CCC GCG CCT TCT GCA CCG GCT CCG GCG CCG CCA CCC GCC GCC TCC CGC        265
Pro Ala Pro Ser Ala Pro Ala Pro Ala Pro Pro Pro Ala Ala Ser Arg
             35                  40                  45

TCC ATG TTC CTG GCC CTC CTG GGG CTG GGA CTG GGC CAG GTG GTC TGC        313
Ser Met Phe Leu Ala Leu Leu Gly Leu Gly Leu Gly Gln Val Val Cys
         50                  55                  60

AGC ATC GCT CTG TTC CTG TAC TTT CGA GCG CAG ATG GAT CCT AAC AGA        361
Ser Ile Ala Leu Phe Leu Tyr Phe Arg Ala Gln Met Asp Pro Asn Arg
     65                  70                  75

ATA TCA GAA GAC AGC ACT CAC TGC TTT TAT AGA ATC CTG AGA CTC CAT        409
Ile Ser Glu Asp Ser Thr His Cys Phe Tyr Arg Ile Leu Arg Leu His
 80                  85                  90                  95

GAA AAC GCA GGT TTG CAG GAC TCG ACT CTG GAG AGT GAA GAC ACA CTA        457
Glu Asn Ala Gly Leu Gln Asp Ser Thr Leu Glu Ser Glu Asp Thr Leu
                100                 105                 110

CCT GAC TCC TGC AGG AGG ATG AAA CAA GCC TTT CAG GGG GCC GTG CAG        505
Pro Asp Ser Cys Arg Arg Met Lys Gln Ala Phe Gln Gly Ala Val Gln
            115                 120                 125

AAG GAA CTG CAA CAC ATT GTG GGG CCA CAG CGC TTC TCA GGA GCT CCA        553
Lys Glu Leu Gln His Ile Val Gly Pro Gln Arg Phe Ser Gly Ala Pro
        130                 135                 140

GCT ATG ATG GAA GGC TCA TGG TTG GAT GTG GCC CAG CGA GGC AAG CCT        601
Ala Met Met Glu Gly Ser Trp Leu Asp Val Ala Gln Arg Gly Lys Pro
    145                 150                 155

GAG GCC CAG CCA TTT GCA CAC CTC ACC ATC AAT GCT GCC AGC ATC CCA        649
Glu Ala Gln Pro Phe Ala His Leu Thr Ile Asn Ala Ala Ser Ile Pro
160                 165                 170                 175

TCG GGT TCC CAT AAA GTC ACT CTG TCC TCT TGG TAC CAC GAT CGA GGC        697
Ser Gly Ser His Lys Val Thr Leu Ser Ser Trp Tyr His Asp Arg Gly
                180                 185                 190

TGG GCC AAG ATC TCT AAC ATG ACG TTA AGC AAC GGA AAA CTA AGG GTT        745
Trp Ala Lys Ile Ser Asn Met Thr Leu Ser Asn Gly Lys Leu Arg Val
            195                 200                 205
```

```
AAC CAA GAT GGC TTC TAT TAC CTG TAC GCC AAC ATT TGC TTT CGG CAT      793
Asn Gln Asp Gly Phe Tyr Tyr Leu Tyr Ala Asn Ile Cys Phe Arg His
            210                 215                 220

CAT GAA ACA TCG GGA AGC GTA CCT ACA GAC TAT CTT CAG CTG ATG GTG      841
His Glu Thr Ser Gly Ser Val Pro Thr Asp Tyr Leu Gln Leu Met Val
            225                 230                 235

TAT GTC GTT AAA ACC AGC ATC AAA ATC CCA AGT TCT CAT AAC CTG ATG      889
Tyr Val Val Lys Thr Ser Ile Lys Ile Pro Ser Ser His Asn Leu Met
240                 245                 250                 255

AAA GGA GGG AGC ACG AAA AAC TGG TCG GGC AAT TCT GAA TTC CAC TTT      937
Lys Gly Gly Ser Thr Lys Asn Trp Ser Gly Asn Ser Glu Phe His Phe
            260                 265                 270

TAT TCC ATA AAT GTT GGG GGA TTT TTC AAG CTC CGA GCT GGT GAA GAA      985
Tyr Ser Ile Asn Val Gly Gly Phe Phe Lys Leu Arg Ala Gly Glu Glu
            275                 280                 285

ATT AGC ATT CAG GTG TCC AAC CCT TCC CTG CTG GAT CCG GAT CAA GAT     1033
Ile Ser Ile Gln Val Ser Asn Pro Ser Leu Leu Asp Pro Asp Gln Asp
            290                 295                 300

GCG ACG TAC TTT GGG GCT TTC AAA GTT CAG GAC ATA GAC TGAGACTCAT      1082
Ala Thr Tyr Phe Gly Ala Phe Lys Val Gln Asp Ile Asp
            305                 310                 315

TTCGTGGAAC ATTAGCATGG ATGTCCTAGA TGTTTGAAAA CTTCTTAAAA AATGGATGAT   1142

GTCTATACAT GTGTAAGACT ACTAAGAGAC ATGGCCCACG GTGTATGAAA CTCACAGCCC   1202

TCTCTCTTGA GCCTGTACAG GTTGTGTATA TGTAAAGTCC ATAGGTGATG TTAGATTCAT   1262

GGTGATTACA CAACGGTTTT ACAATTTTGT AATGATTTCC TAAGAATTGA ACCAGATTGG   1322

GAGAGGTATT CCGATGCTTA TGAAAAACTT ACACGTGAGC TATGGAAGGG GGTCACAGTC   1382

TCTGGGTCTA ACCCCTGGAC ATGTGCCACT GAGAACCTTG AAATTAAGAA GATGCCATGT   1442

CATTGCAAAG AAATGATAGT GTGAAGGGTT AAGTTCTTTT GAATTGTTAC ATTGCGCTGG   1502

GACCTGCAAA TAAGTTCTTT TTTTCTAATG AGGAGAGAAA ATATATGTA TTTTTATATA   1562

ATGTCTAAAG TTATATTTCA GGTGTAATGT TTTCTGTGCA AAGTTTTGTA AATTATATTT   1622

GTGCTATAGT ATTTGATTCA AAATATTTAA AAATGTCTCA CTGTTGACAT ATTTAATGTT   1682

TTAAATGTAC AGATGTATTT AACTGGTGCA CTTTGTAATT CCCCTGAAGG TACTCGTAGC   1742

TAAGGGGGCA GAATACTGTT TCTGGTGACC ACATGTAGTT TATTTCTTTA TTCTTTTTAA   1802

CTTAATAGAG TCTTCAGACT TGTCAAAACT ATGCAAGCAA AATAAATAAA TAAAAATAAA   1862

ATGAATATCT TGAATAATAA GTAGGATGTT GGTCACCAGG TGCCTTTCAA ATTTAGAAGC   1922

TAATTGACTT TAGGAGCTGA CATAGCCAAA AAGGATACAT AATAGGCTAC TGAAAATCTG   1982

TCAGGAGTAT TTATGCAATT ATTGAACAGG TGTCTTTTTT TACAAGAGCT ACAAATTGTA   2042

AATTTTGTTT CTTTTTTTTC CCATAGAAAA TGTACTATAG TTTATCAGCC AAAAAACAAT   2102

CCACTTTTTA ATTTAGTGAA AGTTATTTTA TTATACTGTA CAATAAAAGC ATTGTTTCTG   2162

AATGGCATTT TTTGGTACTT AAAAATGGC                                    2191
```

(2) INFORMATION FOR SEQ ID NO: 2:

(i) SEQUENCE CHARACTERISTICS:
        (A) LENGTH: 316 amino acids
        (B) TYPE: amino acid
        (D) TOPOLOGY: linear (ii) MOLECULE TYPE: protein (xi) SEQUENCE DESCRIPTION: SEQ ID NO: 2:

-continued

```
Met Arg Arg Ala Ser Arg Asp Tyr Gly Lys Tyr Leu Arg Ser Ser Glu
 1               5                   10                  15

Glu Met Gly Ser Gly Pro Gly Val Pro His Glu Gly Pro Leu His Pro
            20              25                  30

Ala Pro Ser Ala Pro Ala Pro Ala Pro Pro Ala Ala Ser Arg Ser
            35          40              45

Met Phe Leu Ala Leu Leu Gly Leu Gly Leu Gly Gln Val Val Cys Ser
 50              55                  60

Ile Ala Leu Phe Leu Tyr Phe Arg Ala Gln Met Asp Pro Asn Arg Ile
 65              70              75                  80

Ser Glu Asp Ser Thr His Cys Phe Tyr Arg Ile Leu Arg Leu His Glu
            85                  90              95

Asn Ala Gly Leu Gln Asp Ser Thr Leu Glu Ser Glu Asp Thr Leu Pro
            100             105             110

Asp Ser Cys Arg Arg Met Lys Gln Ala Phe Gln Gly Ala Val Gln Lys
            115             120             125

Glu Leu Gln His Ile Val Gly Pro Gln Arg Phe Ser Gly Ala Pro Ala
    130             135             140

Met Met Glu Gly Ser Trp Leu Asp Val Ala Gln Arg Gly Lys Pro Glu
145             150             155             160

Ala Gln Pro Phe Ala His Leu Thr Ile Asn Ala Ala Ser Ile Pro Ser
            165             170             175

Gly Ser His Lys Val Thr Leu Ser Ser Trp Tyr His Asp Arg Gly Trp
            180             185             190

Ala Lys Ile Ser Asn Met Thr Leu Ser Asn Gly Lys Leu Arg Val Asn
        195             200             205

Gln Asp Gly Phe Tyr Tyr Leu Tyr Ala Asn Ile Cys Phe Arg His His
    210             215             220

Glu Thr Ser Gly Ser Val Pro Thr Asp Tyr Leu Gln Leu Met Val Tyr
225             230             235             240

Val Val Lys Thr Ser Ile Lys Ile Pro Ser Ser His Asn Leu Met Lys
            245             250             255

Gly Gly Ser Thr Lys Asn Trp Ser Gly Asn Ser Glu Phe His Phe Tyr
            260             265             270

Ser Ile Asn Val Gly Gly Phe Phe Lys Leu Arg Ala Gly Glu Glu Ile
        275             280             285

Ser Ile Gln Val Ser Asn Pro Ser Leu Leu Asp Pro Asp Gln Asp Ala
        290             295             300

Thr Tyr Phe Gly Ala Phe Lys Val Gln Asp Ile Asp
305             310             315
```